United States Patent [19]

Marsh et al.

[11] 4,195,077

[45] * Mar. 25, 1980

[54] DETERGENT COMPOSITIONS COMPRISING MODIFIED PROTEINS

[75] Inventors: Robert A. Marsh, Newcastle upon Tyne; Gordon J. Mackie, Cramlington; Peter Hale, Whitley Bay, all of England

[73] Assignee: The Procter & Gamble Company, Cincinnati, Ohio

[*] Notice: The portion of the term of this patent subsequent to Sep. 19, 1995, has been disclaimed.

[21] Appl. No.: 919,192

[22] Filed: Jun. 26, 1978

Related U.S. Application Data

[63] Continuation of Ser. No. 534,914, Dec. 20, 1974, Pat. No. 4,115,548.

[30] Foreign Application Priority Data

Jan. 18, 1974 [GB] United Kingdom ............... 2366/74

[51] Int. Cl.² ............................................. A61K 7/06
[52] U.S. Cl. ............................... 424/70; 252/DIG. 2; 252/DIG. 3; 252/DIG. 13; 252/545; 252/550; 252/551; 252/554; 252/558; 260/117; 424/168; 424/170; 424/359; 424/365; 424/DIG. 2

[58] Field of Search ................... 424/DIG. 2, 70, 359, 424/168, 170, 365; 260/117; 252/DIG. 2, DIG. 3, DIG.13, 545, 550, 551, 554, 558

[56] References Cited

U.S. PATENT DOCUMENTS

| | | | |
|---|---|---|---|
| 1,965,008 | 7/1934 | Sponsel et al. | 260/117 |
| 3,340,153 | 9/1967 | Kast | 424/365 |
| 3,548,056 | 12/1970 | Eigen et al. | 424/171 |
| 3,642,977 | 2/1972 | Hewitt | 424/70 |
| 3,738,913 | 6/1973 | Johnsen et al. | 424/70 X |
| 3,787,337 | 1/1974 | Goodwin | 424/70 X |

FOREIGN PATENT DOCUMENTS 1122076 7/1968 United Kingdom ................. 424/47

OTHER PUBLICATIONS

Schimmel Briefs, No. 358, 2 pp., Schimmel & Co., Newburgh, N.Y., Jan., 1965.

*Primary Examiner*—Joseph E. Evans
*Assistant Examiner*—Vera C. Clarke

[57] ABSTRACT

Compositions are provided which protect keratinous material such as skin and hair from the deleterious effects of detergents and adverse climatic conditions. Said compositions contain a modified protein and a surface active agent.

4 Claims, No Drawings

DETERGENT COMPOSITIONS COMPRISING MODIFIED PROTEINS

This is a continuation of application Ser. No. 534,914, filed Dec. 20, 1974, now U.S. Pat. No. 4,115,548.

BACKGROUND OF THE INVENTION

This invention relates to compositions which protect keratinous material, such as skin or hair, from the deleterious effects of detergents and from adverse climatic conditions.

The compositions of the invention accordingly help to maintain the keratinous material in good condition. The invention also relates to a method of treating keratin.

The deleterious effects of compositions containing surfactants upon keratin are well known. These effects are caused, it is thought, by penetration of the surfactant into the keratin surface leading to "leaching out" of oils and moisturizing components essential for good condition of the keratin. This surfactant penetration and "leaching out" of essential oils also affects the ability of the keratin, particularly in the case of skin, to retain water within the tissue and this again leads to poor condition of the keratinous material.

Many attempts have been made in the past to provide compositions for maintaining or improving the condition of skin and hair. The application of protein to skin and hair as cosmetic treatments probably antedates recorded history. Casein, in the form of milk, has been used as a time honored beautifier and more recently has been recommended for use in toilet soaps. U.S. Pat. No. 3,548,056 issued Dec. 15, 1970, described the inclusion of partially degraded proteins having a gel strength of zero Bloom grams in detergent compositions and lotions for application to skin such as dishwashing liquids, etc. Copending commonly assigned U.S. Ser. No. 394,589 filed Sept. 5, 1973, now U.S. Pat. No. 3,898,186 discloses liquid detergent compositions containing nonionic surfactants and unmodified gelatins having a molecular weight of at least 12,500, an iso-electric point between about pH 4.5 and about pH 9.2 and a gel strength between 25 and 300 Bloom grams.

OLS No. 2,151,739 and OLS No. 2,151,740 describe certain fatty derivatives of low molecular weight aminolysates suitable for use in shampoos. British Pat. No. 1,122,076 describes the preparation of low molecular weight alcohol soluble protein esters suitable for use in hair spray formulations. Various low molecular weight polypeptides or modified polypeptides are commercially available and recommended for use in cosmetic and shampoo formulations, for instance Hydro Pro 220, Hydro Pro 330, Maypon 4C marketed by the Stepan Chemical Company; Wilson X250, Wilson X1000 and Wilson Aqua Pro marketed by the Wilson Chemical Company. However, none of these materials has proven to be as effective in protecting keratin from the action of detergents as compositions of the present invention, and this is particularly true when the proteins are incorporated in the detergent composition itself. It has been suggested that the emolliency of detergent compositions can be improved by addition of fatty or oily materials but, when used in dishwashing liquids, this usually leads to loss of foaming power or to aesthetic changes which are generally considered undesirable by consumers.

It is an object of the present invention to provide protein-containing compositions which are particularly effective in protecting keratinous material, such as skin or hair, from the deleterious effects of detergents and from adverse climatic conditions, which are effective even when applied to keratin in foaming detergent solutions and which result in no appreciable loss of foaming or cleaning power for detergent solutions containing them.

SUMMARY OF THE INVENTION

According to one aspect of the present invention, a composition for protecting keratinous material from the deleterious effects of detergent and other harsh environments comprises an effective amount of a modified protein, as hereinafter defined, having a molecular weight greater than 5000 and an isoionic point greater than pH 6, the modified protein being incorporated in a compatible carrier additionally comprising a surface active agent.

In this specification a modified protein means a product, other than a derived protein, obtained in one or more stages by chemical or biochemical modification of a precursor protein, a precursor protein being a non-enzymic protein chosen from natural, derived, synthetic or biosynthetic proteins, and a derived protein being the product of hydrolytic, ammoniolytic, enzymic or thermal degradation of a protein material.

According to a further aspect of the invention, there is provided a method of protecting keratinous material from the deleterious effects of detergent and other harsh materials, the method comprising treating keratin with a composition or with an aqueous solution or dispersion of a composition defined herein.

DESCRIPTION OF THE INVENTION

The preferred modified proteins for use in the compositions and method of the present invention, have functional species formed as a result of the modification chosen from one or more of:

C—W—Q; N—X—Q; O—Y—Q; S—Z—Q wherein

C, N, O and S represent carbon nitrogen, oxygen and sulphur atoms respectively, (which atoms are part of the precursor protein), —Z— represents a direct link or carbonyl —Y— represents —Z— sulphonyl or phosphonyl groups —X— represents —Y— or C=NR groups —W— represents, —X—, —NX, —OY— or —SZ— groups and Q represents —$R^1$, —$SR^1$, —$OR^1$, —$NR_2$, —$SR_2^+$, —$NR_3^+$ wherein R represents a hydrogen atom or —$R^1$ and wherein $R^1$ represents one or more alkyl, alkenyl, aryl, cyclo alkyl or heterocyclyl moities, the alkyl or alkenyl moities optionally being interrupted by heteroatoms or functional moities such as dyes, fluorescers, etc. and optionally being substituted with nonionic or cationic radicals, and wherein R has no more than twenty co-adjacent carbon atoms in the alkyl, or alkenyl moieties.

Of course, in a given modified protein, these species need not be all identical. In addition, the various R groups may be the same or different.

Of the above modified proteins, preferred are those proteins in which $R^1$ has the formula

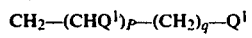

$CH_2$—$(CHQ^1)_p$—$(CH_2)_q$—$Q^1$ in which $Q^1$ is —A, —SA, —OA, —NA$_2$, —SA$_2$+, —NA$_3$+ or O(C=O)A$^1$, in which A is a hydrogen atom or A$^1$ and in which A$^1$ is an alkyl or alkenyl moiety comprising up to 20 carbon atoms, p is 0 or 1 and q is from 0 to (5-p).

In general, R$^1$ will contain no more than eight carbon atoms and up to two heteroatoms, which may be the same or different. Preferred classes of modified protein falling within the above definitions are those in which R$^1$ is represented by:

1. CH$_2$—CHOH—(CH$_2$)$_r$—H in which r is from 0 to 6
2. CH$_2$—(CH$_2$)$_r$—H in which r is from 0 to 7
3.

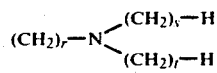

in which r is from 1 to 4 and s, t are from 0 to 3.

The protein modification may be carried out by the normal methods used in preparing proteins having functional substituents. In general, the reactive centers at which modification is performed are protein side-chains which comprise acidic or basic groups, such as carboxylic acid, amino, sulphydryl, aliphatic or phenolic hydroxy groups, imidazole or guanidino groups, or which contain a reactive aromaric rings, as in tyrosine. A preferred modified protein has, as substituents, carboxylic ester or amide groups derived from the carboxylic acid groups of the unmodified substrate. The ester may be obtained from the protein and the appropriate alcohol by suspending the protein in the anhydrous alcohol at a temperature between 0° C. and 25° C. and at an acid concentration of 0.02 to 0.10 M for several days. Alternatively, -hydroxy-alkyl esters may be prepared by reaction of the protein with an epoxide, for example, but-1-ene oxide. Esterified products may also be prepared by reaction with diazoacetic esters or amides. Amides may be produced from the protein carboxylic acid groups by reaction with a water-soluble carbodiimide and an amine. This, simultaneously may lead to modification of phenolic groups of tyrosine or sulphydryl groups of cysteins, giving O-aryl isoureas and S-alkyl isothioureas respectively.

In other embodiments of the invention, the proteins may be acylated or alkylated via amino, hydroxy, or sulphydryl groups. Acylation may be performed by using the appropriate acid anhydried of N-carboxy anhydride. In the latter case, this results in acylation predominantly at amino groups. In the former case, if the acid anhydride is cyclic, the modification leads to acidic substituents which should be neutralized, for instance by esterification. Reactions analogous to acylation may also be performed. Thus e-amino groups of proteins may be replaced selectively by the more basic guanidino groups by treatment with O-alkyl isourea or S-alkyl isothiourea.

Sulfonate ester or sulfonamide derivatives of proteins may be prepared, for instance by reaction of protein hydroxy or amino groups with sulfonyl halides. These modified proteins can, in turn, be used to prepare further modifications by cleavage of the alkyl-oxygen bond of the sulfonate. In this way, hydroxy groups may be replaced, for instance by S-alkyl groups.

Other routes are also available for producing alkylated or arylated proteins. Thus S-alkylation or N-alkylation of sulfhydryl amino groups may be performed by nucleophilic substitution on haloacetates of haloacetamides, or by addition of unsaturated carbon bonds which are conjugated with, for instance, cyanide, as in acrylonitrile or with an amido group as in maleimides. N-alkylation may also be performed by sodium borohydride reduction of the imines formed by condensation of protein amine groups with aliphatic aldehydes or ketones. Arylation of sulfhydryl, amino or hydroxy groups may be performed by nucleophilic substitution of halogen, particularly fluorine, in activated halobenzene derivatives.

The proteins of the compositions of the invention may be modified in numerous other ways. For instance, proteins are susceptible to electrophilic substitution reactions, thus permitting modification of cysteins to cystines by reaction with an iodine donor followed by an alkyl mercaptan. Substitution of the aromatic ring of tyrosine by nitro groups, using tetranitromethane as the nitrating agent, or by diazonium groups is also possible. In addition, the guanidino groups of arginine may be modified by reaction with 1,2 dicarbonyl derivatives such as cyclohexane dione or phenylglyoxal.

The precursor proteins suitable for use, after modification in the compositions of the invention, may be chosen from natural, derived, synthetic or biosynthetic proteins.

Typical natural proteins include intracellular proteins and globular proteins such as those present in blood plasma and milk. Derived proteins may be obtained from many sources, for instance by hydrolytic, ammoniolytic, thermal or enzyme degradation of globular or structural proteins such as keratin, collagen, fibrinogen, myosin, whey, egg white, casein or vegetable proteins such as those obtained from cereals, soybean curd or the protein-rich residues from seed-oil manufacture. A particularly suitable derived protein is gelatin which is the product of hydrolysis (usually acid or base catalyzed) of collagen from skin or bones and may have an average molecular weight varying from 5,000 to 200,000 and even higher. Other highly suitable precursor proteins include whole casein and soybean protein; synthetic proteins such as polylysine, and proteins obtained from unicellular micro-organisms such as bacteria.

It will be appreciated that the molecules of a protein vary widely in their size and complexity and that the molecular weight of a protein is necessarily an imprecise quantity. The molecular weight of a protein may be specified by defining the molecular weight distribution of the molecules of the protein, but it is usual to define, instead, the average molecular weight of the protein sample because it is an average molecular weight which is measured by most physical techniques. Such an average is only an approximate guide, however, to the actual molecular weight distribution of the sample. Also, it should be appreciated that the average molecular weight as measured may vary from one measuring technique to another. Commonly, so called number averaged molecular weights are obtained by measurements of osmotic pressure, rates of diffusion etc. while weight averaged molecular weights are measured, for instance, by ultracentrifuge techniques. In this specification, the method generally employed for determining average protein molecular weights makes use of viscometric measurements of buffered protein solutions. The intrinsic viscosity of a buffered protein solution is known to be primarily dependent upon the overall length of the protein coil and to be relatively independent of the nature of the side-chain and end groups of the protein. There is, therefore, a relationship between intrinsic viscosity, and average molecular weight, M, of the protein which may be expressed as $$[\eta] = K \cdot M^a \quad \text{Staudinger's Equation.}$$

where K and a are constants for a particular source of protein, eg. gelatin derived from calf skin (see The Macromolecular Chemistry of Gelatin, page 72, Arthur Veis, NY Academic (Press), 1964). The intrinsic viscosity is the reduced specific viscosity at infinite dilution of the protein solution, and is defined with respect to actual viscosities measured in a viscometer as follows;

$$\text{relative viscosity } \eta = \frac{\text{measured viscosity of protein in buffered solution}}{\text{rel measured viscosity of buffered solution}}$$

$$\text{specific viscosity } \eta \, sp. = \eta_{rel} - 1$$

$$\text{reduced specific viscosity} = \frac{\eta \, sp}{\text{conc}(c) \text{ of protein solution}}$$

$$\text{intrinsic viscosity} = \lim_{c > o} \left( \frac{\eta \, sp}{c} \right)$$

The constants, K and a, used in evaluating molecular weights of modified calf-skin derived gelatin, were taken as follows (after J. Bello, H. R. Bello and J. R. Vinograd, Biochimica Et Biophysica Acta, 57, 222–9, (1962)

$$K = 2.9 \times 10^{-4}$$

$$a = 0.62$$

The precursor and modified proteins of the present invention have average molecular weights greater than 5000. More particularly, their molecular weights are preferably greater than about 10,000, more preferably greater than 15,000 and generally will be in the range 20,000 to 200,000.

Of the total molecular weight of the modified protein, it is preferred that at least the major fraction is derived from the precursor protein. Desirably, the precursor protein provides between 80% and 99% preferably between 90% and 96% of the total molecular weight of the modified protein.

Protein molecules, having both acidic and basic side chains, are charged both in acidic and basic solutions and thus are amphoteric in nature. The number of such acidic and basic residues in a protein molecule may be measured by titration with a monobasic strong acid (eg. dilute nitric acid) or base (eg. sodium hydroxide solution) and the results are conventionally recorded in millimoles per gram, the number of millimoles of acid or base required to neutralize 1 gm. of the protein. Modified proteins of the present invention have a basic side chain content preferably greater than 0.1 millimoles/gm., more preferably greater than 0.5 millimoles/gm. and desirably greater than 0.8 millimoles/gm. They have an acidic side chain content, preferably, less than 0.5 millimoles/gm. more preferably less than 1.1 millimoles/gm. and desirably less than 0.8 millimoles/gm.

The modified proteins of the present invention have, preferably, proportionately fewer anionic side chains and more nonpolar or cationic side chains than the corresponding unmodified proteins from which they are derived. Modification thus leads, in general, to an increase in hydrophobicity and may lead to an increase in isoionic point pH—the pH at which equal concentrations of protein anions and cations exist in solution.

Preferably, the modified or precursor proteins for use in the compositions of the invention have an isoionic point pH greater than 6.5, more preferably greater than 7.2 and desirably greater than 8.0.

The isoionic point pH of the protein referred to above may differ slightly from the isoelectric point pH of the protein, though usually the differences are small. The isoelectric point is determined by the anion/cation balance of all the ions of the sample being measured, including non-protein ions; the isoionic point on the other hand, is determined by the anion/cation balance of the protein ions alone. The isoionic point pH may be determined in the following manner.

Amberlite acid resin (IR 120) and base resin (IR 400) are washed with several volumes of water, filteres, and mixed in the ratio 0.4:1. A 1½ wt. % protein solution (20 mls) is prepared with minimum warming, allowed to cool to constant temperature and the resin mixture (4.2 g) added, the solution is stirred for five minutes, the mixture filtered and the pH of the filtrate is the isoionic point pH of the protein.

The optimum choice of protein for any particular composition depends to a certain extent, upon the pH of the composition in use, i.e. the pH of the carrier upon application to keratin. This in-use pH may, depending upon the type of application, be the pH of the composition itself, or be the pH of an aqueous solution or dispersion of the composition at a concentration of use which may be as little as 0.01%.

Regarding those compositions comprising modified proteins, it is preferred that the pH of the composition or of an aqueous solution or dispersion of the composition at in-use concentration, be less than (pI+2) in which PI is the isoionic point pH of the modified protein. More preferably this in-use pH is less than (pI+0.5) desirably less than (pI−0.7) and more desirably less than (PI−1.4). In addition, modified proteins having a pI greater than 0.6 may be satisfactorily be used at a pH between (pI+2) and pI.

Regarding those compositions of the invention comprising precursor proteins, it has previously been stated that the pH of the composition or of an aqueous solution of dispersion of the composition at in-use concentration must be less than (pI−0.7). Preferably also, this in-use pH is less than (pI−1.4) and generally less than pH 7.

The in-use pH of the compositions of the invention may vary widely, of course, depending upon the purpose and manner of use of the compositions. Liquid or cream compositions designed for shampoos, hand creams, or cosmetic lotions are generally applied directly to skin or hair, and the in-use pH of the composition itself. This may be any pH in the range, generally, from 4 to 9. Detergent compositions such as liquid dishwashing compositions, bathing compositions and heavy duty granular or liquid detergents are usually used in a large excess of water, and the in-use pH is the pH of an aqueous solution of the composition at a concentration generally in the range from 0.01% to 2 wt. %. Builder free detergent compositions used, for instance, as light duty liquids will have an in-use pH of about 7; built heavy duty detergents generally have an in-use pH in the alkaline range up to a pH of about 11. Soap bar compositions are applied to skin as an aqueous solution or dispersion of the soap bar ingredients at a concentration, generally in the range from 5 to 15 wt. %. The pH of the soap dispersion may vary, depending upon the type of soap bar employed, from a pH of 5.5 to about 9.5.

The preferred compositions of the present invention have an in-use pH in the range from 4 to 11, more preferably in the range of from 5 to 9.5, and most preferably in the range of from 5.5 to 7.5.

The modified proteins of the present invention are preferably made by modification of protein precursor side chains comprising free carboxylic acid groups or free basic, especially primary amino, groups. In particular, modification of acid groups preferably takes the form of oxyalkylation and esterification (correspond to the substitution of

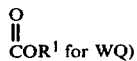

or amidation (corresponding to the substitution of

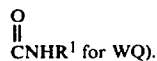

Modification of the basic groups, on the other hand, preferably takes the form of alkylation (corresponding to the substitution of —$R^1$ for XQ). It should be noted that acylation of, for instance, primary amino groups destroys the basic character of such groups, the general effect being in the absence of other kinds of modification being to lower the isoionic point pH of the protein to the region 4.5 to 5.5: N-acylation is therefore preferably not employed as a mode of modification unless there is some other compensating modification which raises the pI of the N-acylated protein to above 6.

Particularly preferred modified proteins in the present invention include esterification or hydroxyalkylation products of high molecular weight gelatins derived from the acid or base hydrolysis of materials such as animal skin or bones. Such modified proteins have proportionately fewer carboxylic acid groups and more carboxylic ester groups than the unmodified proteins. Lower alkyl or hydroxylkyl ester derivatives are preferred. They may be prepared, simply by acid catalyzed esterification with the appropriate alcohol, in which case reaction takes place primarily at the protein carboxylic acid functions, or, alternatively, they may be prepared by treatment with an alkylene oxide, in which case esterification may be accompanied by hydroxyalkylation of other reactive species, for example, primary amino groups. The extent of such N-hydroxyalkylation depends primarily on the pH conditions employed. If the pH of the reaction medium is held in the acid region during the course of the reaction, then the degree of N-hydroxyalkylation is rather less than if the pH is allowed to rise during the reaction. The effect of N-hydroxyalkylation is to lead to an increase in the hydrophobicity of the protein but to a decrease in the isoionic point of the protein. The net effect on conditioning effectiveness is, therefore, relatively minor compared to the effect of esterification on conditioning effectiveness. Preferably, the degree of modification is such that at least 5% more, preferably 20% and desirably at least 35% of the free acidic aside chains of the protein are esterified. The modified proteins may be present in the compositions of the invention in an amount up to 50% but generally in an amount between 1% and 10%, preferably between 2% and 6% by weight of the composition. They are thus effective keratin-conditioning agents even in relatively low concentrations.

Surfactant materials which may be used in the compositions of the invention can be selected from water soluble soap and synthetic anionic, nonionic, cationic, zwitterionic and amphoteric detergents described as follows. Preferably, the surfactants are foaming detergents or emulsifiers.

A. Anionic Soap and Non-Soap Synthetic Detergents

This class of detergents includes ordinary alkali soaps such as the sodium, potassium, ammonium alkyl amonium and alkylolammonium salts of higher fatty acids containing from about 8 to 24 carbon atoms and preferably from about 10 to about 20 carbon atoms. Suitably fatty acids can be obtained from natural sources such as, for instance, from plant or animal esters (e.g. palm oil, coconut oil, babassu oil, soybean oil, castor oil, tallow, whate and fish oils, grease, lard, and mixtures thereof). The fatty acids also can be synthetically prepared (e.g. by the oxidation of petroleum or by hydrogenation of carbon monoxide by the Fischer Tropsch process). Resin acids are suitable such as rosin and those resin acids in tall oil. Naphthenic acids are also suitable. Sodium and potassium soaps can be made by direct saponification of the fats and oils or by the neutralization of the free fatty acids which are prepared in a separate manufacturing process. Particularly useful are the sodium, potassium, and triethanolium salts of the mixtures of fatty acids derived from coconut oil and tallow, ie. sodium or potassium tallow and coconut soap.

This class of detergents also includes water-soluble salts, particularly the alkali metal salts of organic sulfuric reaction products having in their molecular structure an alkyl radical containing from about 8 to about 22 carbon atoms and a sulfonic acid or sulfuric acid ester radical. (Included in the term alkyl is the alkyl portion of higher acyl radicals). Examples of this group of synthetic detergents which form a part of the preferred compositions of the present invention are the alkali metal, e.g. sodium or potassium alkyl sulfates, especially those obtained by sulfating the higher alcohols (8 to 18 carbon atoms) produced by reducing the glycerides of tallow or coconut oil; the alkali metal olefin sulfonates of from 8 to 24 carbon atoms described, for example, in U.S. Pat. No. 3,332,880 issued July 25, 1967 to Phillip E. Pflaumer and Adriaan Kessler; and the alkali metal alkyl glyceryl ether sulfonates, especially those ethers of the higher alcohols derived from tallow and coconut oil; other anionic detergents include the alkali metal alkylbenzene sulfonates, in which the alkyl group contains from about 9 to about 15 carbon atoms, including those of the types described in U.S. Pat. Nos. 2,220,099 and 2,477,383 (the alkyl radical can be a straight or branched aliphatic chain); sodium coconut oil fatty acid monoglyceride sulfates and sulfonates; salts of alkyl phenol ethylene oxide ether sulfate with about 1 to about 12 units of ethylene oxide per molecule and in which the alkyl radicals contain from 8 to about 18 carbon atoms; the reaction product of fatty acids esterified with isethionic acid and neutralized with sodium hydroxide where, for example, the fatty acids is oleic or derived from coconut oil; sodium or potassium salts of fatty acid amide of a methyl tauride in which the fatty acids, for example are derived from coconut oil; sodium or potassium beta-acetoxy- or beta-acetamido-alkane-sulfonates where he alkane has from 8 to 22 carbon atoms; and others known in the art, a number specifically set forth in U.S. Pat. Nos. 2,286,921, 2,486,922, and 2,396,278.

Other synthetic anionic detergents useful herein are alkyl ether sulfates. These materials have the formula $R^2O(C_2H_4O)_xSO_3M$ wherein $R^2$ is alkyl or alkenyl of about 8 to about 24 carbon atoms, x is 1 to 30, and M is a salt forming cation selected from alkali metal, ammonium, dimethyl-, trimethyl-, triethyl-, dimethanol-, diethanol-, trimethanol- and triethanol-ammonium salts.

The alkyl ether sulfates of the present invention are condensation products of ethylene oxide and monohydric alcohols having about 8 to about 24 carbon atoms. Preferably, $R^2$ has 14 to 18 carbon atoms. The alcohols can be derived from fats, e.g. coconut oil or tallow, or can be synthetic. Lauryl alcohol and straight chain alcohols derived from tallow, or can be synthetic. Lauryl alcohol and straight chain alcohols derived from tallow are preferred herein. Such alcohols are reacted with 1 to 12 and especially 6, molar proportions of ethylene oxide and the resulting mixture of molecular species, having, for example an average of 6 moles of ethylene oxide per mole of alcohol, is sulfated and neutralized.

Specific examples of alkyl ether sulfates of the present invention are sodium coconut alkyl ethylene glycol ether sulfate; lithium tallow alkyl triethylene glycol ether sulfate; and sodium tallow alkyl hexaoxyethylene sulfate.

Preferred herein for reasons of excellent cleaning properties and ready availability oare the alkali metal coconut- and tallow-alkyl oxyethylene ether sulfates having an average of about 1 to about 10 oxyethylene moieties. The alkyl ether sulfates are described in U.S. Pat. No. 3,332,876.

B. Nonionic Synthetic Detergents

Nonionic synthetic detergents may be broadly defined as compounds produced by the condensation of alkylene oxide groups (hydrophilic in nature) with an organic hydrophobic compound, which may be aliphatic or alkyl aromaric in nature. The length of the hydrophilic or polyoxyalkylene radical which is condensed with any particular hydrophobic group can be readily adjusted to yield a water-soluble compound having the desired degree of balance between hydrophilic and hydrophobic elements.

For example, a well known class of nonionic synthetic detergents is made available on the market under the trade name of "Pluronic". These compounds are formed by condensing ethylene oxide with a hydrophobic base formed by the condensation of propylene oxide with propylene glycol. The hydrophobic portion of the molecule which, of course, exhibits water insolubility, has a molecular weight of from about 1500 to 1800. The addition of polyoxyethylene radicals to this hydrophobic portion tends to increase the water solubility of the molecule as a whole and the liquid character of the product is retained up to the point where polyoxyethylene content is about 50% of the total weight of the condensation product. Other suitable nonionic synthetic detergents include:

1. The polyethylene oxide condensates of alkyl phenol, e.g. the condensation products of alkyl phenols having an alkyl group containing from about 6 to 12 carbon atoms in either a straight chain or branched chain configuration, with ethylene oxide, the said ethylene oxide being present in amounts equal to 5 to 25 moles of ethylene oxide per mole of alkyl phenol. The alkyl substituent in such compounds may be derived from polymerized propylene, diisobutylene, octene, or nonene, for example.

2. Those derived from the condensation of ethylene oxide with the product resulting from the reaction of propylene oxide and ethylene diamine. For example compounds containing from about 40% to about 80% polyoxyethylene by weight and having a molecular weight of from about 5,000 to about 11,000 resulting from the reaction of ethylene oxide groups with a hydrophobic base constituted of the reaction product of ethylene diamine and excess propylene oxide. Said base having a molecular weight of the order of 2,500 and 3,000 are satisfactory.

3. The condensation product of aliphatic alcohols having from 8 to 24 carbon atoms, in either straight chain or branched chain configuration with ethylene oxide, e.g. a coconut alcoholethylene oxide condensate having from 5 to 30 moles of ethylene oxide per mole of coconut alcohol, the coconut alcohol fraction having from 10 to 14 carbon atoms.

4. Nonionic detergents include nonyl phenol condensed with either about 10 or about 30 moles of ethylene oxide per mole of phenol and the condensation products of coconut alcohol with an average of either about 5.5 or about 15 moles of ethylene oxide per mole of alcohol and the condensation product of about 15 moles of ethylene oxide with one mole of tridecanol. Other examples include dodecylphenol condensed with 12 moles of ethylene oxide per mole of phenol; dinonylphenol condensed with 15 moles of ethylene oxide per mole of phenol; dodecyl mercaptan condensed with 10 moles of ethylene oxide per mole of mercaptan; bis-(N-2-hydroxyethyl) lauramide; nonyl phenol condensed with 20 moles of ethylene oxide per mole of nonyl phenol; myristyl alcohol condensed with 10 moles of ethylene oxide per mole of myristyl alcohol; lauramide condensed with 15 moles of ethylene oxide per mole of lauramide and di-isooctylphenol condensed with 15 moles of ethylene oxide.

5. A detergent having the formula $R^3R^4R^5N$ O(amine oxide detergent) wherein $R^3$ is an alkyl group containing from about 10 to about 28 carbon atoms, from 0 to about 2 hydroxy groups and from 0 to about 5 ether linkages, there being at least one moiety of $R^3$ which is an alkyl group containing from about 10 to about 18 carbon atoms and 0 ether linkages, and each $R^4$ and $R^5$ are selected from the group consisting of alkyl radicals and hydroxyalkyl radicals containing from 1 to about 3 carbon atoms.

Specific examples of amine oxide detergents include: dimethyldodecylamine oxide, dimethyltetradecylamine oxide, ethylmethyltetradecylamine oxide, cetyldimethylamine oxide, dimethylstearylamine oxide, cetylethylpropylamine oxide, diethyldodecylamine oxide, diethyltetradecylamine oxide, dipropyldodecylamine oxide, bis-(2-hydroxyethyl) dodecylamine oxide, bis-(2-hydroxyethyl)-3-dodecoxy-1-hydroxypropylamine oxide, (2-hydroxypropyl) methyltetradecylamine oxide, dimethyloleylamine oxide, dimethyl-(2-hydroxydodecyl) amine oxide, and the corresponding decyl, hecadecyl and octadecyl homologs of the above compounds.

6. A detergent having the formula

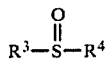

wherein $R^3$ and $R^4$ are defined above. Specific examples of sulfoxide detergents include dodecyl methyl sulfoxide, tetradecyl methyl sulfoxide, 3-hydroxytridecyl methyl sulfoxide, 3-methoxytridecyl methyl sulfoxide, 3-hydroxy-4-dodecoxybutyl methyl sulfoxide, octadecyl 2-hydroxyethyl sulfoxide, dodecylethyl sulfoxide.

7. The ammonia, monoethanol and diethanol amides of fatty acids having an acyl moiety of from about 8 to about 18 carbon atoms. These acyl moieties are normally derived from naturally occurring glycerides, e.g. coconut oil, palm oil, soybean oil and tallow but can be derived synthetically, e.g. by the oxidation of petroleum, or by hydrogenation of carbon monoxide by the Fischer Tropsch process.

C. Ampholytic Synthetic Detergents

Ampholytic synthetic detergents can be broadly described as derivatives of aliphatic or aliphatic derivatives of heterocyclic secondary and tertiary amines, in which the aliphatic radical may be straight chain or branched and wherein one of the aliphatic substituents contains from about 8 to 18 carbon atoms and at least one contains an anionic water solubilizing group, e.g. carboxy, sulfo, or sulfato. Examples of compounds falling within this definition are sodium 3-(dodecylamino)-propionate, sodium 3-(dodecylamino)propane-1-sulfonate, sodium 2-(dodecylamino) ethylsulfate, sodium 2-dimethyl amino) octadecanoate, disodium 3-(N-carboxymethyl dodecylamino) propane-1-sulfonate, disodium octadecyl-iminodiazetate, sodium 1-carboxymethyl-2-undecyl imidazole, and sodium N,N-bis-(2-hydroxyethyl)-2-sulfato 3-dodecoxypropylamine.

D. Zwitterionic Synthetic Detergents

Zwitterionic synthetic detergents can be broadly described as derivatives of aliphatic quaternary ammonium and phosphonium or tertiary sulfonium compounds, in which the cationic atom may be part of a heterocyclic ring, and in which the aliphatic radical may be straight chain or branched and wherein one of the aliphatic substituents contains from about 3 to 18 carbon atoms, and at least one aliphatic substituent contains an anionic water-solubilizing group, e.g. carboxy, sulfo, or sulfato. Examples of compounds falling within this definition are 3-(N,N-dimethyl-N-hexadecyl-ammonio)-2-hydroxypropane-1-sulfonate, 3-(N,N-dimethyl-N-hexadecylammonio)-propane-1-sulfonate, 2-(N,N-dimethyl-N-dodecylammonio) acetate, 3-(N,N-dimethyl-N-dodecylammonio) propionate, 2-(N,N-dimethyl-N-octadecylammonio)ethyl sulfate, 2-(S-methyl-S-tert. hexadecyl-sulfonio)ethane-1-sulfonate, 3-(S-methyl-S-dodecylsulfonio) propionate, 4-(S-methyl-S-tetradecylsulfonio) butyrate, 1-(2-hydroxy-ethyl) 2-undecyl imidazolium-1-acetate, 2-(trimethylammonio)octadecanoate, and 3-(N,N-bis-(2l -hydroxyethyl)-N-octadecylammonio)-2-hydroxy propane-1-sulfonate and 3-(N,N dimethyl-N-1-methyl alkyl ammonio)-2-hydroxy propane-1-sulfonate, wherein alkyl averages 13.5 to 14.5 carbon atoms in length. Some of these detergents are described in the following U.S. Pat. Nos. 2,129,264; 2,178,353; 2,774,786; 2,813,898; and 2,828,332.

E. Cationic Detergents

Cationic detergents include those having the formula $R^6-N(R^7{}_+)_3An$—wherein $R^6$ is an alkyl chain containing from about 8 to about 20 carbon atoms, each $R^7$ is selected from the group consisting of alkyl and alkanol groups containing from 1 to 4 carbon atoms and benzyl groups there being normally no more than one benzyl group and two $R^2$ groups can be joined by either a carbon-carbon ether, or imino linkage to form a ring structure, and An represents a halogen atom, sulfate group, nitrate group or other psuedohalogen group. Specific examples are coconut alkyl trimethyl amine chloride, dodecyl dimethyl benzyl bromide and dodecyl methyl morpholino chloride.

The soap and non-soap anionic, nonionic and zwitterionic detergent surfactants mentioned above can be used as the sole surface-active agents or the various examples may be mixed when used in the practice of the invention. Especially preferred are anionic and nonionic surface active agents. The amount of surface active agent incorporated in the preparations depends upon the intended use of the particular formulation. It will relate to the weight of the preparation to as a whole, whether it is applied directly to skin, e.g. as a cosmetic lotion, or the concentration at which it will be used as a solution in for example, dishwashing water or bath water. In most cases a content within the range of 0.1% to 90% by weight of the preparation is suitable. More particularly, detergent compositions for cleaning purposes will generally comprise between about 5 and 50% by weight of surface active agent, while cosmetic compositions will generally comprise between 0.1 and 10% by weight of surface active agent.

The invention is applicable to a variety of compositions which may come into contact with keratin in the normal course of use, for example, diswashing liquids, hand or face creams, body lotions, hair shampoos, bathing compositions, heavy duty detergent compositions, hard surface cleaning compositions, bar soaps, etc. The physical form of the composition may vary equally widely, from granular solids, through gels and creams to viscous or mobile liquid compositions. Dishwashing compositions are generally liquid and comprise mixtures of water and foaming detergents. Granular detergent compositions on the other hand, may contain little or no free water. Cosmetic and related compositions will generally have a base comprising a mixture of water, emulsifier and oil, and the physical constitution of these compositions will be that of oil-in-water emulsions. It is also envisaged, however, that cosmetic like compositions of the invention may be in the form of gels comprising the modified protein, a surfactant, and water and optionally containing a preservative. Other cosmetic like compositions however, may contain little or no free water but comprise a mixture of the modified protein, oil and foaming surfactant. Such compositions are particularly suitable as bathing compositions.

The preferred liquid or granular detergent compositions for use e.g. as heavy duty detergents, dishwashing compositions or shampoos, comprise between 5 and 50% by weight of foaming detergent. More especially the foaming detergent is seleeted from:

a. Up to 45% weight of a water soluble hydrocarbon sulfate of the general formula $R^2O(C_2H_4O)_nSO_3M$ wherein $R^2$ is a straight or branched saturated or unsaturated aliphatic hydrocarbon radical having from 8 to 24 carbon atoms, or a benzene radical substituted with an aliphatic, straight or branched hydrocarbon group having from 8 to 18 carbon atoms; n is from 1 to 12; and M is an alkali-metal, ammonium, dimethyl-trimethyl, triethyl-dimethanol-, diethanol-, trimethanol- and triethanol-ammonium salt;

b. up to 45% by weight of a water soluble hydrocarbon sulfonate of the general formula $R^2SO_3M$;

c. up to 45% by weight of a water soluble hydrocarbon sulfate of the general formula $R^2OSO_3M$;

d. up to 40% by weight of the ammonia, monoethanol and diethanol amides of a fatty acid having an aryl moiety of from 8 to 18 carbon atoms;

e. up to 40% by weight of the condensation product of from 3 to 25 moles of an alkylene oxide, preferably ethylene or propylene oxide, and one mole of an organic, hydrophobic compound, aliphatic or alkyl aromatic in nature, the latter having from 8 to 24 carbon atoms.

Another component which may be included in the compositions of the invention, is a water soluble buffer material. The purpose of the buffer is to establish the pH range which optimizes the conditioning effectiveness of these compositions. Suitable acidic buffers may be chosen from acetic-, citric-, malic-, gluconic-, maleic-, lactic-, tartaric-, propionic-, butyric-, malonic-, polymaleic-, polyitaconic-, glutoric-, citraconic acid; benzene pentacarboxylic- and hexacarboxylic acid; succinic acid, ethylene diamine tetra-acetic acid and nitrilo acetic acid; and the weakly acidic salts thereof. When the protein has a pI greater than about pH 9, the optimum in-use pH range is about 7 or higher, and this may require the use of basic buffer materials. These may be chosen from the basic salts of the organic acids mentioned above, or from more traditional alkaline inorganic buffer materials such as alkali metal phosphates, polyphosphates, carbonates, silicates and borates. Acidic buffer materials are generally used in proportions up to 15%, preferably, up to 5% by weight of a composition. Alkaline buffer materials may be used up to about 40% by weight in a granular detergent composition, or up to about 5% by weight in a liquid detergent composition.

The liquid detergent or gel compositions of the invention generally comprise a carrier based upon water and/or a water soluble solvent. Suitable solvents include $C_{2-8}$ mono and di-alcohols, e.g. ethanol, butanol, methyl propanol-1 and -2, amylol or pentanol, butanediol, toluol, benzyl carbinol, ethyleleglycol monobutyl ether, propyleneglycol propyl ether, diethyleneglycol dimethyl ether. They are generally present in amounts up to 15% by weight of the composition. Additional components of liquid detergent compositions include foam boosters, such as higher alkyl amine oxides, and alkylolamides of $C_{10}$–$C_{14}$ carboxylic acids, thickeners, preservatives, opacifiers, perfumes, dyes, fluorescers, tarnish inhibitors, bactericides, hydrophobic oily materials and hydrotropes. Commonly employed hydrotropes include conventional lower alkylaryl sulfonates such as sodium and potassium toluene sulfonate, xylene sulfonate benzene sulfonate and cumeme sulfonate. Urea and lower alkanol hydrotropes such as methanol, ethanol, propanol and butanol may also be used.

Hydrophobic oily materials suitable for use in the present invention include animal, vegetable and mineral oils and waxes, for example beeswax, spermaceti and carnauba wax; fatty alcohols such as stearyl, myristyl and cetyl alcohol; fatty esters and partial esters such as isopropyl myristate, glyceryl monostearate; fatty acids such as stearic acid; lanolin and cholestrol derivatives; and silicone oils. The compositions of the invention particularly the cosmetic creams or lotions, may also comprise components designed to enhance the moisturizing effectiveness of the compositions. Suitable components include lower aliphatic alcohols having from about 2 to about 6 carbon atoms and 2 to 3 hydroxy groups, for example 1,4 butanediol, 1,2-propylene glycol, glycerine. Other suitable components include urea or urea derivatives such as guanidine, pyrrolidone or allantoin. Solid granular detergent compositions may contain foam enhancers, foam depressents bleaches, anti-redeposition agents, enzymes, enzyme and bleach activators, fluorescers, builders and other normal components of granular detergent compositions. Solid compositions in bar form may also contain additives such as fatty acids, salts, skin creams and oil.

Oxyalkylation of Proteins

The following procedure is typical of methods which may be used for oxyalkylation of proteins. In this instance, the method is described with reference to the oxybutylation of gelatin. Base hydrolysis derived gelatin (10 g) having a molecular weight of about 80,000 and isoionic point pH of about 5.35, was dissolved in water (500 ml) and the pH of the solution was adjusted to 7.5 with sodium hydroxide solution. The solution was heated with stirring at a constant temperature of 27° C. and but-1-ene oxide (65 ml) was added. The reaction was allowed to proceed for a period of 26 hours during which time the pH was held below 8.0 by the addition of sulfuric acid. At the end of this period the isoionic point pH of the hydroxybutylated gelatin as measured by mixed bed ion exchange, was 7.8. After evaporation of excess but-1-ene oxide, the solution was dialysed slowly for 6 hours to remove salts and low molecular material and the modified gelatin was finally obtained by freeze drying. The product was then washed with 1:1 methanol/ether, followed by ether, and was then dessicated to dryness. The hydroxy butylated gelatin had an intrinsic viscosity (measured in a 4.5 pH buffer solution comprising sodium chloride (0.15 m), sodium acetate (0.1 m) and acetic acid (0.1 m) of 0.301 which using the empirical relation of Staudinger and the values of the constants K and a of Bello, Bello and Vinograd, corresponds to an average molecular weight of 73,000. The percentage of esterification of the gelatin, as measured by titration, was 43% while the percentage of N-alkylation measured by Van Slyke determination of primary amino groups, was 61%. The above method, or variations thereof, may be used to prepare modified gelatins having various substituents and physical characteristics. For instance, maintaining the pH of the reaction medium in the acid range diminished the degree of N-hydroxyalkylation which takes place during reaction. Modified gelatins of higher molecular weight may be prepared by using correspondingly higher molecular weight starting materials. Ethylene or propylene oxide may be used in place of but-1-ene oxide to produce the corresponding oxyalkylated derivatives. Other types of proteins may equally be used in place of base-hydrolysis derived gelatin; for instance acid hydrolysis derived gelatins, or proteins such as casein, gliadin, soya bean protein, zein and serum or egg albumins. Other processes may also be used to obtain oxyalkylated derivatives, for example, reaction with anhydrous alkylene carbonates.

Protein Esterification

Protein derivatives in which only the carboxylate groups have been modified may be made according to the following process. Gelatin (10 g) having a gel strength of about 140 Bloom grams, an isoionic point of about 5.3, and ground to 60 mesh size, was stirred at room temperature into a 0.036 N solution of concentrated sulfuric acid (1.76 g) in absolute methanol (1,000 ml). After standing for about 20 hours with occasional shaking, the methanolic solution was decanted from the solid, which was washed with methanol, followed by ether, and was then dried in a dessicator at 0.1 mm Hg pressure. Acid residue were removed from the product by stirring the gelatin in ten times its weight of water while adding 5 N sodium hydroxide until pH 6 was reached. The swollen granules were melted at 40° C. to give a clear liquid which was set to a gel at 4° C. and dried in a current of air. Salts and low molecular materials were removed from the product by autodialysis, after which the product was dried as before.

The isoionic point pH of the methyl ester derivatives of gelatin, as measured by mixed bed ion exchange, was 7.8. Its intrinsic viscosity, measured in a 4.5 pH buffer solution, was 0.31, corresponding to an average molecular weight of 70,000. The percentage of methyl esterification was 44%.

Amine Alkyl Amide Derivatives of Proteins

Protein derivatives having high isoionic point pH values may be made, for instance, by modifying protein carboxylic acid groups to carboxylic acid amino alkyl amide groups as follows:

A solution of N,N-dimethyl ethylene diamine (10 ml) in water (80 ml) was prepared and its pH was adjusted to 4.5 with sulfuric acid. Gelatin (2 g) having a gel strength of about 240 Bloom grams, was added, together with N-cyclohexyl-N-(2-4-B-morpholinyl)-ethyl)-carbodiimide methyl p-toluene sulfonate (4 g.). The pH of the solution was adjusted to 4.8 and the solution was then allowed to stand at about 25° C. for a period of 6½ hours. It was diluted with water and then dialysed slowly for about 14 hours, during which time the pH rose to about 7.5. Finally the product was isolated by freeze drying followed by vacuum drying in a dessicator. The 2-(N,N-dimethyl amino)ethyl amide derivative of gelatin had the following characteristics:
Isoionic point pH = 10.5
Intrinsic viscosity = 0.49
Average molecular weight = 162,000
Percentage of carboxylic acid groups modified = 42%

Skin Conditioning Tests

Conditioning performance was measured in both in-vitro and in-vivo tests, a high degree of correlation between the two test methods being found. The in-vitro test (called the calf-skin occlusivity test) was based upon the rate of water transpiration through a sample of calf-skin brought into contact with a 0.15% aqueous solution of a detergent composition (at 18° hardness) containing the protein. The occulusivity of the protein was measured as the reduction in the rate of water transpiration for the proteinaceous surfactant solution compared with that for water.

The in-vivo test used was hand-immersion testing (HIT). This test used a base of 16 people (32 hands) per product in a multiproduct test, hands were balanced for right hand/left hand differences, so that there were 32 hands per product, 16 right and 16 left. Each person immersed left and right hands in different solutions for three consecutive 10 minute periods in half an hour per day, for 3 weeks, 5 days per week. Treatment solutions were replenished every 10 minutes. Hands were graded on the starting Monday (before immersion) and on each Friday of the test. They were graded on a 0–10 (perfect) overall hand condition scale, a 0–10 (bad) skin scaling scale and a 0–10 (perfect) nail grinding scale. HIT grades for protein/surfactant solutions were determined and are quoted here, on a scale in which an 0.15% aqueous solution of the surfactant of standard II (see Table V) was assigned HIT grades of 0, and a 1 mg/cm$^2$ application of hand care lotion was assigned HIT grades of 100.

EXAMPLES 1 to 13

A number of oxybutylated gelatins, made by the methods described earlier, were compared for providing conditioning benefits from aqueous surfactant solutions. The modified proteins were prepared with varying molecular weights, isoionic points, degrees of O-alkylation, N-alkylation etc. They were then incorparated in the various liquid detergent compositions of Examples 1 to 13 listed in Table 4. Examples 1 to 4 demonstrate the effect (see table 1) of changing molecular weight upon the conditioning performance of oxybutylated gelatins. It can be seen that oxybutylated gelatins having molecular weights in the range 5000 to 200,000 are all effective in providing conditioning benefits from aqueous surfactant solution, but that these benefits are greatest for modified proteins in the higher molecular weight range, i.e. above about 20,000. Proteins having lower molecular weights, about 5000 or even less, still provide a useful level of conditioning benefit however.

Examples 6 to 9 demonstrate the effect of changing protein isoionic point pH upon conditioning performance at a constant pH of application to skin (pH 7). It can be seen that conditioning performance is very sensitive to the isoionic point pH (pI) modified proteins having a pI above 8 and preferably above 8.5 being the most effective for any given molecular weight value.

Performance may be seen to diminish to a certain extent for pI values below the pH of application.

The effect of the level of modified protein in surfactant, is demonstrated by comparison of Example 1, 10 and 11. The optimum level of protein is about 4% by weight of the compositions, there being only minor benefits for increase of protein level to 5% by weight. At a level of incorporation of 2% by weight, however, conditioning benefits were reduced by over 50%.

The conditioning performance of Example 1, 2 and 3 as a function of pH of application to keratin, is outlined in Table 3. The optimum pH range for conditioning effectiveness evidently lies below the isoionic point pH of the protein, conditioning effectiveness generally diminishing for pH values above the isoionic point. In comparsion with the control surfactant solution (Standard 2) however, conditioning benefits persist, at a somewhat lower level, even over the higher pH region.

The final two entries in Table 1, examples 12 and 13 demonstrate the inclusion of the same modified protein used in Example 1, in a surfactant solution based upon paraffin sulphonate and alkyl ether sulphate. While examples 12 and 13 are seen to be rather less effective than most of the earlier examples, it is also evident from the calf skin testing that the compositions of Examples 12 and 13 will be rather more mild than the same liquid detergent compositions (Standard 3) containing no modified protein.

Also included in Table 1 is the hand immersion best data for Examples 1 to 3 and 11. This data shown that those modified proteins having a molecular weight greater than about 15000 and an isoionic point pH greater than about 8, are particularly effective in protecting keratin from the deleterious effects of detergent solutions applied to keratin at about pH 7. In particular, the compositions of Examples 1 to 3 have been shown to provide from dilute aqueous surfactant solutions, at least two-thirds of the conditioning benefit provided by a hand-care lotion applied directly to the skin-surface. Additionally, in five, three-week hand immersion tests, the composition of Example 1 left hands and nails in a significantly better condition at 95% confidence than did the composition of Standard 2.

A further advantage of the above protein containing compositions is that there is substantially no diminution in the volume or stability of foam associated with the detergent composition itself. Furthermore, it has been found that the above compositions have excellent storage stability, and indeed, that the surfactant has the effect of increasing the stability of the protein to hydrolysis, at about pH 7, by a factor of up to about six.

EXAMPLES 14 to 19

Table 2 compares the conditioning performance of various modified proteins incorporated in surfactant compositions as defined in Table 4. Once again, it can be seen that the high molecular weight, high isoionic point modified proteins of the present invention are particularly effective in providing in-vitro occlusivity benefits from aqueous surfactant solutions.

The conditioning performance of the composition of Example 17 as a function of pH of application to keratin is shown in Table 4. This modified protein has a very high isoionic point pH (about 10.5) and is effective across a broad pH range below the isoionic point pH and up to 2 pH units above the isoionic point pH. Effectiveness diminishes for pH of application greater than (pI+2). Unlike most of the other examples, where conditioning performance at pH values below the modified protein pI, is relatively insensitive to the hardness of the treatment solution, the composition of Example 17 is somewhat more effective over this pH range in the absence of free water hardness. Thus at pH 9.3 to 9.5 the calf-skin occlusivity grade is 4.5 at 0° hardness but only 1.5 at 18° hardness.

EXAMPLES 20 to 26

The following examples serve to illustrate, but not to limit, liquid detergent compositions according to the present invention. All percentages indicated are by weight.

EXAMPLES

|  | 20 | 21 | 22 | 23 | 24 | 25 | 26 |
|---|---|---|---|---|---|---|---|
| Dimethyldodecyl amine oxide | 8% | 4% | 2% | 4% | 2% | 4% | 3% |
| Coconut alcohol ethylene oxide (6) condensate | 15 | 7 | 6 | 7 | 2 | 7 | 6 |
| Diethanol $C_{12-16}$ fatty acid amide | 2 |  | 3 |  | 2 |  | 2 |
| Coconut alcohol ethylene oxide (3) sulfate sodium salt |  | 10 | 9 | 14 | 10 | 12 | 14 |
| $C_{13-18}$ paraffin sulfonate, sodium salt |  | 10 | 9 |  | 9 | 10 | 12 |
| $C_{12-13}$ alpha-olefin sulfonate, ammonium salt |  |  |  | 12 |  |  |  |
| Urea | 8 | 6 |  | 10 | 8 | 6 | 10 |
| Ethyl Alcohol | 11 | 13 | 13 | 13 | 13 | 12 | 13 |
| Modified Gelatin* | 2 | 4 | 4 | 4 | 5 | 3 | 4 |

EXAMPLES-continued

|  | 20 | 21 | 22 | 23 | 24 | 25 | 26 |
|---|---|---|---|---|---|---|---|
| Water |  |  |  | Balance |  |  |  |

*Modified Gelatin: hydroxybutyl derivative; molecular weight 25,000; iso-ionionic point 9.1; % of O-alkylated side chains 48; % of N-alkylated side chains 20.

The above compositions are milder to skin and hair than the corresponding compositions containing no modified protein and there is substantially no diminution in the volume or the stability of foam produced by the detergent. Substantially similar cleaning and conditioning performance is obtained when the modified protein in the above example is replaced by the oxybutylation product of casein which has been purified by the Hammarsten method, the modified casein having a pI of 8.8% of O-alkylated side chains of 40% and % of N-alkylated side chains of 61%.

EXAMPLES 27 to 32

|  | 27 | 28 | 29 | 30 | 31 | 32 |
|---|---|---|---|---|---|---|
| Coconut alcohol-ethylene oxide (3) sulfate, ammonium salt | 16 |  | 18 | 18 |  | 12 |
| Coconut alcohol-ethylene oxide (9) sulfate, sodium salt |  | 22 |  |  | 14 |  |
| $C_{13}$-$C_{18}$ paraffin sulfonate, sodium salt | 10 | 8 | 14 | 10 | 5 | 8 |
| $C_{12}$-$C_{14}$ olefin sulfonate, ammonium salt |  | 8 |  |  | 10 |  |
| $C_{10}$-$C_{14}$ alkyl benzene, sodium salt |  |  | 5 |  |  | 14 |
| Modified Gelatin* | 4 | 3 | 4 | 2 | 5 | 3 |
| Ethyl Alcohol | 10 | 11 | 13 | 10 | 13 | 8 |
| Water |  |  | Balance |  |  |  |

*Modified gelatin: hydroxyethyl derivative; molecular weight 80,000; isoionic point pH 8.3; % of O-alkylated side chains 47; % of N-alkylated side chains 40.

Substantially similar cleaning and conditioning performance is obtained when the modified protein is replaced by a methyl, ethyl, propyl or butyl ester of gelatin having a molecular weight of about 80,000 and an isoionic point pH of 8 to 9.5.

EXAMPLE 33

A foaming oil bath having foaming and skin conditioning properties, has the following composition.

|  | Parts by wt. |
|---|---|
| Hexadecyldimethyl amine oxide | 40 |
| Mineral Oil | 56 |
| Water | 1 |
| Oxybutylated gelatin: Molecular wt. 90,000; isoionic point pH 8.8; % of O-alkylated side chains 45; % of N-alkylated side chains 40 | 4 |

EXAMPLE 34

|  | Parts by wt. |
|---|---|
| Real Soap (Tallow/coconut = 50/50) | 78.5 |
| Free Fatty Acid | 7.6 |
| Moisture | 9.3 |
| Skin Cream | 0.5 |
| N,N dimethyl ethylene diamine derivative of gelatin, isoionic point pH 10.5; molecular wt. 100,000; % of O-alkyla- | 4.0 |

-continued

| | Parts by wt. |
|---|---|
| tion 42 | |

EXAMPLE 35

A moisturizing hand cream has the following composition.

| | Parts by wt. |
|---|---|
| Stearic acid | 12 |
| Mineral Oil | 2 |
| Cetyl Alcohol | 0.6 |
| Glycerol | 6.0 |
| Triethanolamine | 1.5 |
| Borax | 0.9 |
| Glyceryl monostearate | 2.0 |
| Methyl p-hydroxy benzoate | 0.25 |
| Modified Gelatin* | 5.0 |
| Water | to 100.0 |

*Modified Gelatin: hydroxypropyl derivative; molecular weight 80,000; isoionic point pH 9.2; % of O-alkylated side chains 35; % of N-alkylated side chains 61.

EXAMPLE 36

A proteinized hair cream rinse has the following composition.

| | Parts by wt. |
|---|---|
| Tegamine S-13 | 4 |
| Phosphoric acid (85%) | 0.6 |
| Methyl p-hydroxy benzoate | 0.2 |
| Glyceryl monostearate | 1.5 |
| Modified casein* | 8.0 |
| Water | to 100 parts |

"Tegamine" S-13 is a dialkylaminoalkyl stearamide marketed by the Goldschmidt Chemical Company. Modified casein*: oxybutyl derivative; isionic point pH 8.8, % of O-alkylated side chains 40; % of N-alkylated side chains 61.

EXAMPLE 37

A cosmetic gel for application to face and hands, has the following composition.

| | Parts by wt. |
|---|---|
| Ethyl alcohol | 10 |
| Methyl p-hydroxy benzoate | 0.3 |
| Modified gelatin* | 15 |
| Water | to 100 |

*Modified Gelatin: oxybutyl derivative; isoionic point pH 9.6; molecular weight 15,000; % of O-alkylated side chains 24; % of N-alkylated side chains 43.

EXAMPLE 38

A dishwashing liquid has the following composition:

| | Parts by wt. |
|---|---|
| Coconut alcohol-ethylene oxide (12) sulfate ammonium salt | 18.75 |
| Coconut alcohol sulfate, ammonium salt | 5.8 |
| Sodium alkyl glyceryl ether sulfonate (where the alkyl is derived from "middle-cut" coconut alcohols and has the following approximate composition: 2% $C_{10}$; 66% $C_{12}$; 23% $C_{14}$; 9% $C_{16}$) | 4.0 |
| Coconut alkyl dimethyl amine oxide (wherein the coconut is middle cut) | 5.0 |
| Potassium chloride | 2.5 |
| Potassium toluene sulfate | 0.5 |
| Citric acid | 0.1 |
| Hydrogen chloride | 0.81 |
| Ammonium xylene sulfate | 5.0 |
| Ethanol | 8.75 |
| Modified Gelatin: Hydroxybutyl derivative; molecular weight 25,000; isoionic point 9.1; % of O-alkylated side chains 48; % of N-alkylated side chains 20 | 4.0 |
| Water | to 100 |

TABLE 1

Conditioning Performance of Oxybutylated Gelatins at pH 7

| EXAMPLE | wt% of protein in composition | % of o-alkylation | % of N-alkylation | isoionic point pH | Molecular Weight | In-Vitro occlusivity | Hand Immersion Testing | |
|---|---|---|---|---|---|---|---|---|
| | | | | | | | Overall Cond. | Skin Scaling Condition |
| 1 | 4 | 45 | 40 | 8.8 | 190,000 | 8.2 | 64 | 44 |
| 2 | 4 | 44 | 39 | 9.0 | 80,000 | 7.7 | 61 | 53 |
| 3 | 4 | 48 | 20 | 9.1 | 25,000 | 6.4 | 68 | 42 |
| 4 | 4 | 24 | 43 | 9.6 | 15,000 | 4.6 | — | — |
| 5 | 4 | — | 17 | 9.1 | 9,000 | 3.1 | — | — |
| 6 | 4 | 47 | 30 | 8.9 | 80,000 | 8.3 | — | — |
| 7 | 4 | 49 | 59 | 7.9 | 100,000 | 5.9 | — | — |
| 8 | 4 | 39 | — | 6.9 | 80,000 | 4.7 | — | — |
| 9 | 6 | 56 | 52 | 6.2 | 80,000 | <1 | — | — |
| 10 | 5 | 45 | 40 | 8.8 | 190,000 | 7.8 | — | — |
| 11 | 2 | 45 | 40 | 8.8 | 190,000 | 5.3 | 31 | 33 |
| 12 | 4 | 45 | 40 | 8.8 | 190,000 | 2.3 | — | — |
| 13 | 4 | 45 | 40 | 8.8 | 190,000 | 2.5 | — | — |
| STANDARDS | | | | | | | | |
| 1 | — | — | — | — | — | 0 | — | — |
| 2 | — | — | — | — | — | −6.1 | 0 | 0 |
| 3 | — | — | — | — | — | −3.6 | 0 | −12 |

TABLE 2

Conditioning Performance of Various Modified Proteins at pH 7

| EXAMPLE | Modifying Reagent/Protein | wt% of protein in composition | % of o-Alkylation | % of N-Alkylation | Isionic Point pH | Molecular Weight | in Vitro occlusivity |
|---|---|---|---|---|---|---|---|
| | Ethylene oxide/gelatin | 4 | 47 | 40 | 8.3 | 80,000 | 6.4 |
| 15 | Propylene oxide/gelatin | 4 | 35 | 61 | 9.2 | 80,000 | 4.4 |
| 2 | But-1-ene oxide/gelatin | 4 | 44 | 39 | 9.0 | 80,000 | 7.7 |

TABLE 2-continued

Conditioning Performance of Various Modified Proteins at pH 7

| EXAMPLE | Modifying Reagent/Protein | wt% of protein in composition | % of o-Alkylation | % of N-Alkylation | Isionic Point pH | Molecular Weight | in Vitro occlusivity |
|---|---|---|---|---|---|---|---|
| 16 | Methanol/gelatin | 4 | 35 | — | 9.0 | 100,000 | 2.7 |
| 17 | N,N dimethyl ethylene diamine/gelatin | 4 | 42 | 7 | 10.5 | 100,000 | 3.0 |
| 18 | But-1-ene oxide/casein | 4 | 40 | 61 | 8.8 | — | 3.2 |
| 19 | But-1-ene oxide/soybean protein | 4 | — | — | 8.5 | — | 6.0 |
| STANDARDS | | | | | | | |
| 4 | Superpro 16 C | 6 | — | — | 5–6 | 1,000 | >−7 |
| 5 | Hydropro 230 | 6 | — | — | 6.5 | 300 | +0.1 |
| 6 | Crotein SPC | 6 | — | — | 5–5.5 | 10,000 | −6.1 |
| 7 | Crotein SPO | 6 | — | — | 5–5.5 | 2,000 | −1.2 |
| 8 | Wilson X250 | 6 | — | — | 6 | 1,000 | −3.4 |
| 9 | Wilson X1000 | 6 | — | — | 5 | 10,000 | −6.7 |

TABLE 3

Conditioning Performance as Function of pH of Application

| pH of application | Standard 2 | Ex. 1 | Ex. 2 | Ex. 3 | Ex. 17 | Standard 10 |
|---|---|---|---|---|---|---|
| 4.0 | — | — | — | — | — | — |
| 4.5 | — | — | — | — | — | — |
| 5.0 | −8.5 | 2.5 | — | 1.3 | — | −5.0 |
| 5.5 | — | — | — | — | — | — |
| 6.0 | −5.3 | 5.7 | — | — | — | — |
| 6.5 | — | — | — | — | — | — |
| 7.0 | −6.1 | 8.2 | 7.7 | 6.4 | 3.0 | −6.1 |
| 7.5 | — | — | — | — | — | — |
| 8.0 | −6.2 | — | — | — | — | — |
| 8.5 | — | −1.5 | 1.5 | — | 1.5 | — |
| 9.0 | −6.5 | — | — | −2.7 | 1.4 | — |
| 9.3 | −7.3 | −6.2 | −1.3 | — | 1.5 | — |
| 10.0 | — | −6.0 | −3.7 | — | 1.0 | — |
| 10.5 | — | — | — | — | — | — |
| 11.0 | −5.2 | — | — | — | 3.5 | — |
| 11.5 | — | — | — | — | 3.8 | — |
| 12.0 | — | — | — | — | — | — |
| 12.5 | −1.1 | — | — | — | −1.2 | — |

TABLE 4

| | EXAMPLES | | | | | | | | | | | STANDARDS | | | |
|---|---|---|---|---|---|---|---|---|---|---|---|---|---|---|---|
| | 1,4, 15,18, 19 | 4,7 14,16, 17 | 2 | 3,5 | 8 | 9 | 10 | 11 | 12 | 13 | 1 | 2 | 3 | 4,5, 6,7, 8,9 | 10 |
| Ammonium linear $C_{12}$–$C_{14}$ alkyl benzene sulfonate | 18.4 | 18.4 | 18.4 | 18.4 | 18.4 | 18.4 | 18.4 | 18.4 | — | — | — | 18.4 | — | 18.4 | 18.4 |
| Sodium linear $C_{12}$–$C_{14}$ alcohol sulfate including 3 ethylene oxide moities | 18.4 | 18.4 | 18.4 | 18.4 | 18.4 | 18.4 | 18.4 | 18.4 | 13.5 | 18.4 | — | 18.4 | 13.5 | 18.4 | 18.4 |
| Sodium $C_{14}$ paraffin sulfonate | — | — | — | — | — | — | — | — | 27.0 | 18.4 | — | — | 27.0 | — | — |
| Lauric monoethanolamide | 2.0 | 2.0 | 2.0 | 2.0 | 4.5 | 4.5 | 4.5 | 4.5 | — | 2.0 | — | 4.5 | — | 2.0 | 2.0 |
| Urea | 10.0 | 6.0 | 6.0 | 10.0 | — | — | — | 8.0 | 6.0 | 12.0 | — | — | — | — | 10.0 |
| Ethyl alcohol | 13.0 | 13.0 | 13.0 | 15.0 | 13.0 | 13.0 | 13.0 | 13.0 | 7.0 | 10.0 | — | 13.0 | 7.0 | 13.0 | 13.0 |
| Protein* | 4.0 | 4.0 | 4.0 | 4.0 | 4.0 | 6.0 | 5.0 | 2.0 | 4.0 | 4.0 | — | — | — | 6.0 | 4.0 |
| Water | To 100 | To 100 | To 100 | To 100 | To 100 | To 100 | To 100 | To 100 | To 100 | To 100 | 100 | To 100 | To 100 | To 100 | To 100 |

*Protein incorporated as granules comprising about 10% water

What is claimed is:

1. A composition for protecting keratinous material from the deleterious effects of detergent or from adverse climatic conditions, said composition comprising
   (a) an effective amount of a modified protein selected from the group consisting of oxyethylated, oxypropylated, oxybutylated and N,N-dimethyl ethylene diamine modified gelatin, casein, and soy protein, said modified protein having a molecular weight greater than 5,000 and an isoionic point greater than 6;
   (b) from 0.1% to 90% by weight of a surface-active agent; and
   (c) a compatible carrier.

2. The composition as recited in claim 1 in which the composition contains from 1% to 10% by weight of the modified protein.

3. The composition as recited in claim 2 in which the modified protein is oxybutylated gelatin.

4. A method of protecting skin or hair from the deleterious effect of detergent or from adverse climatic conditions, comprising treating the skin or hair with an effective amount of the composition of claim 1 or with a dilute aqueous solution or dispersion thereof.

* * * * *